(12) United States Patent
Baxter et al.

(10) Patent No.: US 7,410,972 B2
(45) Date of Patent: Aug. 12, 2008

(54) COMPOUNDS

(75) Inventors: Andrew Baxter, Loughborough (GB);
Timothy Johnson, Loughborough (GB);
Nicholas Kindon, Loughborough (GB);
Bryan Roberts, Loughborough (GB);
John Steele, Loughborough (GB);
Michael Stocks, Loughborough (GB);
Nicholas Tomkinson, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 502 days.

(21) Appl. No.: 10/499,102

(22) PCT Filed: Dec. 17, 2002

(86) PCT No.: PCT/SE02/02355

§ 371 (c)(1),
(2), (4) Date: Nov. 23, 2004

(87) PCT Pub. No.: WO03/051870

PCT Pub. Date: Jun. 26, 2003

(65) Prior Publication Data

US 2005/0075346 A1    Apr. 7, 2005

(30) Foreign Application Priority Data

Dec. 18, 2001  (SE) .................... 0104474
Jul. 5, 2002    (SE) .................... 0202139

(51) Int. Cl.
*A61K 31/4965*  (2006.01)
*C07D 401/00*   (2006.01)
*C07D 403/00*   (2006.01)
*C07D 405/00*   (2006.01)
*C07D 409/00*   (2006.01)
*C07D 411/00*   (2006.01)
*C07D 413/00*   (2006.01)
*C07D 417/00*   (2006.01)
*C07D 419/00*   (2006.01)

(52) U.S. Cl. .............. 514/255.05; 544/405

(58) Field of Classification Search ............ 514/255.05; 544/405
See application file for complete search history.

(56) References Cited

U.S. PATENT DOCUMENTS 5,962,490 A  * 10/1999  Chan et al. .................. 514/380
6,420,567 B1 *  7/2002  Wu et al. ..................... 548/245
6,632,829 B2 * 10/2003  Wu et al. ..................... 514/361

FOREIGN PATENT DOCUMENTS

| EP | 0713875 A1    | 5/1996 |
|----|---------------|--------|
| WO | 98/13366 A1   | 4/1998 |
| WO | 2004/007472 A1| 1/2004 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Chantry and Burgess, "Chemokines in Allergy" Current Drug Topics—Inflammation & Allergy, vol. 1, pp. 109-116 (2002).*

* cited by examiner

*Primary Examiner*—Zachary C Tucker
(74) *Attorney, Agent, or Firm*—Morgan, Lewis & Bockius LLP

(57) ABSTRACT

The invention provides N-pyrazinyl-thienylsulphonamides of formula (I) for use in the treatment of chemokine mediated diseases. Particularly inflammatory diseases, such as asthma (I)

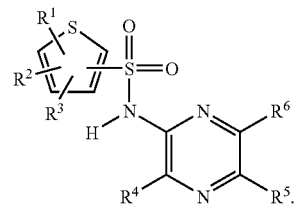

16 Claims, No Drawings

COMPOUNDS

The present invention relates to a sulphonamide compound, processes and intermediates used in their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small-secreted molecules are a growing superfamily of 8-14 kDa proteins characterised by a conserved four cysteine motif. At the present time, the chemokine superfamily comprises three, groups exhibiting characteristic structural motifs, the Cys-X-Cys (C—X—C), Cys-Cys (C-C) and Cys-$X_3$-Cys (C—$X_3$—C) families. The C—X—C and C-C families have sequence similarity and are distinguished from one another on the basis of a single-amino acid insertion between the NH-proximal pair of cysteine residues. The C—$X_3$—C family is distinguished from the other two: families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils. Examples include human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β. Thymus and Activation Regulated Chemokine (TARC, CCL17) and Macrophage Derived Chemokine (MDC, CCL22). The C—$X_3$—C chemokine (also known as fractalkine) is a potent chemoattractant and activator of microglia in the central nervous system (CNS) as well as of monocytes, T cells, NK cells and mast cells.

Studies have demonstrated that the actions of chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C—X—C family) and $CX_3CR1$ for the C—$X_3$—C family. These receptors represent good targets for drug development since agents which modulate these receptors would be useful in the treatment of disorders and diseases such as those mentioned above.

U.S. Pat. No. 5,962,490 discloses a series of sulphonamide compounds said to be useful for treating endothelin mediated diseases. There is no specific disclosure of pyrazine sumphonamides and no mention of chemokine mediated diseases.

The present invention therefore provides a compound of formula (I) and pharmaceutically-acceptable salts or solvates thereof:

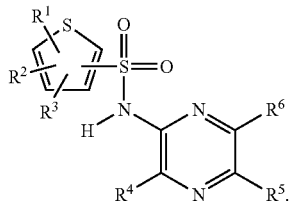

(I)

in which:
$R^1$, $R^2$ and $R^3$ are independently hydrogen, halogen, cyano, $CF_3$, or $C_{1-6}$alkyl;
$R^4$ is halogen, $CO_2R^{12}$,
$C_{1-6}$ alkoxy where the alkyl group may form a 3-6 membered saturated ring or may be substituted with 1-3 fluorine atoms or a cyano group;
$C_{3-6}$ alkenyloxy or $C_{3-6}$ alkynyloxy where either may be optionally substituted with hydroxy or $NR^{14}R^{15}$;
$OC_{1-6}$ alkyl-X—$C_{1-6}$ alkyl where the alkyl groups may form a 3-6-membered saturated ring;
$OC_{1-6}$ alkyl$R^{11}$, or $OC_{2-6}$ alkyl-X—$R^{11}$ where the alkyl group may form a 3-6 membered saturated ring and is optionally substituted with 1-3 groups selected from hydroxy, halogen, $NR^{14}R^{15}$, $SR^{13}$, $S(O)_2R^{13}$, $S(O)R^{13}$;
$OC_{1-6}$ alkyl$R^{16}$;
$R^5$ and $R^6$ are independently hydrogen, cyano, halogen, $CO2R^{12}$, $CONR^{14}R^{15}$;
$C_{1-6}$ alkyl optionally substituted by hydroxy, $NR^{14}R^{15}$, or 1-3 fluorines;
$C_{1-6}$ alkyl$R^{11}$ or $XCH(R^{11})C_{1-6}$ alkyl or $XCH(R^{16})C_{1-6}$ alkyl where the alkyl group may be optionally substituted with 1-3 groups selected from hydroxy, and $NR^{14}R^{15}$;
$NR^{14}R^{15}$; $N(R^{11})R^{11}$; X—$(CH_2)qNR^{14}R^{15}$; $(CH_2)nNR^{14}R^{15}$;
$C_{3-6}$ alkynyl or $C_{3-6}$ alkenyl optionally branched and optionally substituted with 1-3 groups selected from hydroxy, cyano, halogen and =O;
$R^{11}$; X—$R^{11}$; X—$R^{12}$; X—$C_{1-6}$alkyl$R^{16}$; X—$R^{16}$; X—$(CH_2)nCO_2R^{12}$; X—$(CH_2)nCONR^{14}R^{15}$; X—$(CH_2)nR^{11}$; X—$(CH_2)nCN$; X—$(CH_2)qOR^{12}$; $(CH_2)nOR^{12}$; $(CH_2)n$—X—$R^{11}$; X—$(CH_2)qNCH(O)NHR^{12}$; X—$(CH_2)qNHC(O)R^{12}$; X—$(CH_2)qNHS(O)_2R^{12}$; X—$(CH_2)qNHS(O)_2R^{11}$; X—$C_{3-6}$alkenyl; X—$C_{3-6}$alkynyl, n is 1, 2, 3, 4 or 5;
q is 2, 3, 4, 5 or 6;
X is $NR^{13}$, O, S, S(O), $S(O)_2$;
$R^{11}$ is an aryl group, or a 5-7 membered-heteraromatic ring containing 1-4 heteroatoms selected from nitrogen, oxygen or sulphur each of which can be optionally substituted by 1-3 groups selected from halogen, $C(O)NR^{14}R^{15}$, $C(O)OR^{12}$, hydroxy, =O, =S, CN, $NO_2$, $NR^{14}R^{15}$, $X(CH_2)qNR^{14}R^{15}$, $(CH_2)nNR^{14}R^{15}$, $(CH_2)nOH$, $SR^{13}$, $S(O)R^{13}$, $S(O)^2R^{13}$ $C_{1-6}$ alkyl-X-$C_{1-6}$ alkyl, $C_{1-6}$ alkyl or $C_{1-6}$ alkoxy where the alkyl group may form a 3-6 membered ring or is optionally substituted with 1-3 groups selected from hydroxy, halogen, $NR^{14}R^{15}$, $SR^{13}$, $S(O)R^{13}$, $S(O)_2R^{13}$;
$R^{12}$ and $R^{13}$ are independently hydrogen or $C_{1-6}$ alkyl where the alkyl group may be substituted with 1-3 fluorine atoms or may form a saturated 3-6 membered ring;
$R^{14}$ and $R^{15}$ are independently hydrogen, $C_{1-6}$ alkyl, $C_{3-6}$ cycloalkyl or $(CH_2)qOH$, or $R^{14}$ and $R^{15}$ together with the nitrogen atom to which they are attached form a 4-8 membered saturated ring containing 1-3 heteroatoms selected from nitrogen, oxygen and sulphur and optionally substituted by $C_{1-6}$ alkyl, $C_{1-6}$ alkyl-OH, or hydroxy, and
$R^{16}$ is a 4-8 membered saturated ring containing 1-3 heteroatoms selected from nitrogen, oxygen or sulphur and optionally substituted with 1-3 groups selected from hydroxy, cyano, halogen and =O.

The term aryl includes phenyl and naphthyl. The term alkyl whether alone or as part of another group, includes straight chain and branched chain alkyl groups. Examples of 5- to 7-membered heteroaromatic ring containing 1 to 4 heteroatoms include thienyl, furanyl, pyrrolyl, imidazolyl, pyridyl, pyrazinyl, pyrimidyl, pyridazinyl; triazinyl, oxazolyl, thiazolyl, isoxazolyl, pyrazolyl, oxadiazolyl, thiadiazolyl, triazolyl and tetrazolyl. Examples of saturated 4 to 8-membered rings containing 1 to 3 heteroatoms include morpholine, piperidine and azetidine. Substituents on any rings can be present in any suitable ring position including suitable substituents on nitrogen atoms.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Preferably the thienyl moiety is linked to the sulphonamide at the 2-position of the thiophene ring.

Preferred halogen groups for $R^1$, $R^2$ and $R^3$ are chloro or bromo. Preferably $R^1$, $R^2$ and $R^3$ are all hydrogen or two are hydrogen and the other is chloro, bromo or methyl. More preferably $R^2$ and $R^3$ are hydrogen and $R^1$ is chloro at the 5-position of the thienyl ring.

For the group $R^4$ examples of $C_{3-6}$ alkenyloxy include $OCH_2CH{=}CH_2$, examples of $C_{3-6}$ alkynyloxy include $OCH_2CCH$, examples of $OC_{1-6}$ alkyl-$O$—$C_{1-6}$ alkyl include $OCH_2CH_2OMe$, examples of $OC_{1-6}$ alkyl$R^{11}$ include $OCH_2R^{11}$, and examples of $OC_{1-6}$ alkyl$R^{16}$ include $OCH_2$ pyrrolidine.

Preferred groups for $R^4$ include $C_{1-6}$ alkoxy such as methoxy and ethoxy, phenoxy, 2-furanylmethoxy, bromo, 2-methoxyethoxy, (5-methyl-3-isoxazolyl)methoxy, 2-pyridylmethoxy, 3-pyridazinylmethoxy, methoxy, 2-(1-imidazolyl)ethoxy and 4-methoxyphenylmethoxy. More preferably $R^4$ is methoxy or pyridylmethoxy. Most preferably $R^4$ is methoxy.

For $R^5$ and $R^6$ examples of $NR^{14}R^{15}$ includes morpholine, pyrrolidine, $NMe_2$, $NHCH_2CH_2OMe$, and the groups below:

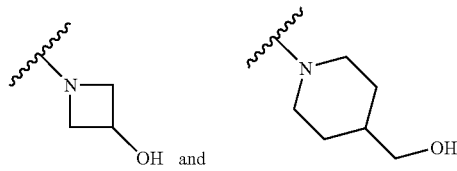

Examples of $X$—$(CH_2)qNR^{14}R^{15}$ includes $SCH_2CH_2NH_2$ and $SCH_2CH_2NMe_2$, examples of $(CH_2)nNR^{14}R^{15}$ include $CH_2$ morpholine, examples of $X$—$R^{12}$ includes SMe, OMe, OEt, OH, $SO_2Me$, examples of $X$—$C_{1-6}$alkyl$R^{16}$ includes $OCH_2$ pyrrolidine, examples of $X$—$(CH_2)nCO_2R^{12}$ includes $SCH_2CO_2H$, $SCH_2CO_2Me$, $SCH_2CH_2CO_2Me$, examples of $X$—$(CH_2)nCONR^{14}R^{15}$ includes $SCH_2CONH_2$, $SCH_2CONHMe$, $SCH_2CONMe_2$, examples of $X$—$(CH_2)nR^{11}$ includes the groups below:

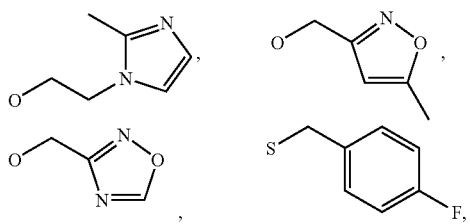

Examples of $X$—$(CH_2)nCN$, includes $SCH_2CN$, examples of $X$—$(CH_2)qOR^{12}$ includes $OCH_2CH_2OMe$, examples of $(CH_2)nOR^{12}$ includes $CH_2OH$, $CH_2OMe$, examples of $X$—$(CH_2)qNHC(O)NHR^{12}$ includes $SCH_2CH_2NHC(O)NHEt$, and examples of $X$—$(CH_2)qNHC(O)R^{12}$ includes $NHCH_2CH_2NHC(O)Me$.

Preferred groups for $R^5$ include hydrogen, halogen such as bromo and chloro, phenyl, $C_{1-6}$ alkyl such as methyl, cyano and 2-aminothanethiol. More preferably $R^5$ is hydrogen, methyl or halogen such bromo or chloro.

Preferred groups for $R^6$ include hydrogen, $C_{1-6}$ alkyl and halogen, more preferably hydrogen, methyl, and chloro.

Preferred compounds of formula (I) include:
N-(5-Bromo-3-methoxy-2-pyrazinyl)-5-chloro-2-thiophenesulphonamide
N-(5-Bromo-3-ethoxy-2-pyrazinyl)-5-chloro-2-thiophenesulphonamide
N-(5-Bromo-3-methoxy-2-pyrazinyl)-4,5-dichloro-2-thiophenesulphonamide
5-Chloro-N-(3-methoxy-5-phenyl-2-pyrazinyl)-2-thiophenesulphonamide
N-(5-Bromo-3-phenoxy-2-pyrazinyl)-5-chloro-2-thiophenesulphonamide
N-(5-Bromo-3-methoxy-2-pyrazinyl)-2-thiophenesulphonamide
N-[5-Bromo-3-(2-furanylmethoxy)-2-pyrazinyl]-5-chloro-2-thiophenesulphonamide
5-Chloro-N-(3,5-dibromo-2-pyrazinyl)-2-thiophenesulphonamide
5-Chloro-N-(3-methoxy-5-methyl-2-pyrazinyl)-2-thiophenesulphonamide
5-Chloro-N-(5-chloro-3-methoxy-2-pyrazinyl)-2-thiophenesulphonamide,
5-Bromo-N-(5-bromo-3-methoxy-2-pyrazinyl)-2-thiophenesulphonamide
5-Chloro-N-(6-chloro-3-methoxy-2-pyrazinyl)-2-thiophenesulphonamide;
3-Bromo-N-(5-bromo-3-methoxy-2-pyrazinyl)-5-chloro-2-thiophenesulphonamide
N-(5-Bromo-3-methoxy-2-pyrazinyl)-3-thiophenesulphonamide
5-Chloro-N-(5,6-dichloro-3-methoxy-2-pyrazinyl)-2-thiophenesulphonamide
5-Chloro-N-[5-bromo-3-(2-methoxyethoxy)-2-pyrazinyl]-2-thiophenesulphonamide
5-Chloro-N-[5-bromo-3-[2-(1-imidazolyl)ethoxy]-2-pyrazinyl]-2-thiophenesulphonamide
5-Bromo-N-(6-chloro-3-methoxy-2-pyrazinyl)-2-thiophenesulphonamide
5-Bromo-N-(5-chloro-3-methoxy-2-pyrazinyl)-2-thiophenesulphonamide
5-Chloro-N-[6-chloro-3-(2-furanylmethoxy)-2-pyrazinyl]-2-thiophenesulphonamide,
5-Chloro-N-[6-chloro-3-(5-methyl-3-isoxazolylmethoxy)-2-pyrazinyl]-2-thiophenesulphonamide
5-Chloro-N-[6-chloro-3-(2-pyridinylmethoxy)-2-pyrazinyl]-2-thiophenesulphonamide
5-Chloro-N-[5-methyl-3-(3-pyridinylmethoxy)-2-pyrazinyl]-2-thiophenesulphonamide
5-Chloro-N-[5-methyl-3-(3-pyridazinylmethoxy)-2-pyrazinyl]-2-thiophenesulphonamide
5-Chloro-N-[3-(2-pyridinylmethoxy)-2-pyrazinyl]-2-thiophenesulphonamide
5-Chloro-N-(3-methoxy-2-pyrazinyl)-2, thiophenesulphonamide
5-Chloro-N-(5,6-dimethyl-3-methoxy-2-pyrazinyl)-2-thiophenesulphonamide.
N-[5-Chloro-3-methoxy-2-pyrazinyl]-5-methyl-2-thiophenesulphonamide,
5-Methyl-N-[5-methyl-3-methoxy-2-pyrazinyl]-2-thiophenesulphonamide
N-[5-{(2-Aminoethyl)sulpanyl}-3-methoxy-2-pyrazinyl]-5-chloro-2-thiophenesulphonamide 5-Chloro-N-[5-cyano-3-methoxy-2-pyrazinyl]-2-thiophene-sulphonamide
N-[5-Bromo-3-(4-methoxybenzyloxy)-2-pyrazinyl]-5-chloro-2-thiophenesulphonamide and pharmaceutically acceptable salts and solvates thereof.

A preferred sub-class of compounds of formula (I) are compounds (IA) where $R^1$, $R^2$ and $R^3$ are independently hydrogen, $C_{1-6}$ alkyl or halogen;

$R^4$ is halogen, $C_{1-6}$ alkoxy or $OR^9$;

$R^5$ and $R^6$ are independently hydrogen, halogen, $C_{1-6}$ alkoxy, $C_{1-6}$ alkylthio, cyano, $R^9$, $OR^9$, $NR^9R^{10}$, $SR^9$, $S(CH_2)_n CO_2H$, $S(CH_2)_n CO_2R^{12}$, $S(CH_2)CONR^{12}R^{13}$, $S(CH_2)_n R^{11}$ or a 5- to 7-membered heteroaromatic or saturated ring containing 1 to 3 heteroatoms selected from nitrogen, oxygen and sulphur, n is 1, 2 or 3;

$R^9$ and $R^{10}$ are independently hydrogen, $C_{1-6}$ alkyl optionally substituted by hydroxy, $C_{1-6}$ alkoxy or $NHCOC_{1-6}$ alkyl, or $R^9$ and $R^{10}$ are optionally substituted aryl, $C_{1-6}$ alkyl-aryl or $C_{1-6}$ alkyl-$R^{11}$ or $R^9$ and $R^{10}$ together with the nitrogen atom to which they are attached form a 4- to 8-membered saturated ring containing 1 to 3 heteroatoms selected from nitrogen, oxygen and sulphur and optionally substituted by $C_{1-6}$ alkyl or $C_{1-6}$ alkyl-OH; and $R^{11}$ is a 5- to 7-membered heteraromatic ring containing 1 to 3 heteroatoms selected from nitrogen, oxygen and sulphur and optionally substituted by $C_{1-6}$ alkyl; and $R^{12}$ and $R^{13}$ are independently hydrogen or $C_{1-6}$ alkyl.

For sub-class (IA) the thienyl moiety is preferably linked to the sulphonamide at the 2-position.

For sub-class (IA) $R^1$, $R^2$ and $R^3$ are independently hydrogen, $C_{1-6}$ alkyl or halogen, preferred halogen groups being chloro or bromo. Preferably $R^1$, $R^2$ and $R^3$ are all hydrogen or two are hydrogen and the other is chloro, bromo or methyl. More preferably $R^2$ and $R^3$ are hydrogen and $R^1$ is chloro at the 5-position of the thienyl ring.

For sub-class (IA) preferred groups for $R^4$ include $C_{1-6}$ alkoxy such as methoxy and ethoxy, phenoxy, 2-furanylmethoxy, bromo, 2-methoxyethoxy, (5-methyl-3-isoxazolyl)methoxy, 2-pyridylmethoxy, 3-pyridazinylmethoxy, methoxy, and 2-(1-imidazolyl)ethoxy.

For sub-class (IA) preferred groups for $R^5$ include hydrogen, halogen such as bromo and chloro, phenyl and $C_{1-6}$ alkyl such as methyl.

For sub-class (IA) preferred groups for $R^6$ include hydrogen, $C_{1-6}$ alkyl and halogen, more preferably hydrogen, methyl and chloro.

For sub-class (IA) preferred compounds include those of examples 1 to 32 exemplified herein, both in free acid form and in the form of pharmaceutically acceptable salts.

According to the invention there is also provided a process for the preparation of compound (I) which comprises reaction of a compound of formula (II):

(II)

where $R^4$, $R^5$ and $R^6$ are as defined in formula (I) or are protected derivatives thereof with a compound of formula (III):

(III)

where $R^1$, $R^2$ and $R^3$ are as defined in formula (I) or are protected derivatives thereof and LG is a leaving group, and optionally thereafter
   removing any protecting groups,
   forming a pharmaceutically acceptable salt.

Preferred leaving groups LG include halogen such as chloro. Preferably the reaction between compounds (II) and (III) is carried out by treating compound (II) with a base such as sodium hydride or potassium tert-butoxide in a suitable solvent such as 1,2-dimethoxyethane or tetrahydrofuran.

Where $R^4$ is $C_{1-6}$ alkoxy where the alkyl group may form a 3-6 membered saturated ring or may be substituted with 1-3 fluorine atoms or a cyano group;

$C_{3-6}$ alkenyloxy or $C_{3-6}$ alkynyloxy where either may be optionally substituted with hydroxy or $NR^{14}R^{15}$;

$OC_{1-6}$ alkyl-X—$C_{1-6}$ alkyl where the alkyl groups may form a 3-6 membered saturated ring;

$OC_{1-6}$ alkyl$R^{11}$, or $OC_{2-6}$ alkyl-X—$R^{11}$ where the alkyl group may form a 3-6 membered saturated ring and is optionally substituted with 1-3 groups selected from hydroxy, halogen, $NR^{14}R^{15}$, $SR^{13}$, $S(O)_2R^{13}$, $S(O)R^{13}$; or $OC_{1-6}$ alkyl$R^{16}$;

compounds of formula (II) can be prepared by treating a compound of the formula (IV), where LG is a leaving group (such as chlorine or bromine):

(IV)

with a compound of formula (V)

$R^4$—H                                                           (V)

in a suitable solvent (such as 1,2-dimethoxyethane, N,N-dimethylformamide or tetrahydrofuran) with a suitable base such as sodium hydride or potassium tert-butoxide at a suitable temperature such as 25° C. to 60° C.

Where $R^4$ is $C_{1-6}$ alkoxy where the allyl group may form a 3-6 membered saturated ring or may be substituted with 1-3 fluorine atoms or a cyano group;

$C_{3-6}$ alkenyloxy or $C_{3-6}$ alkynyloxy where either may be optionally substituted with hydroxy or $NR^{14}R^{15}$;

$OC_{1-6}$ alkyl-X—$C_{1-6}$ alkyl where the alkyl groups may form a 3-6 membered saturated ring;

$OC_{1-6}$ alkyl$R^{11}$, or $OC_{2-6}$ alkyl-X—$R^{11}$ where the alkyl group may form a 3-6 membered saturated ring and is optionally substituted with 1-3 groups selected from hydroxy, halogen, $NR^{14}R^{15}$, $SR^{13}$, $S(O)_2R^{13}$, $S(O)R^{13}$; or $OC_{1-6}$ alkyl$R^{16}$;

compounds of formula (I) can be prepared by treating a compound of the formula (VI), where LG is a leaving group (such as chlorine or bromine):

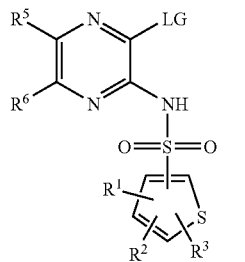
(VI)

with a compound of formula (V)

in a suitable solvent (such as 1,2-dimethoxyethane, N,N-dimethylformamide or tetrahydrofuran) with a suitable base such as sodium hydride or potassium tert-butoxide at a suitable temperature such as 25° C. to 60° C.

Compounds of structure (VIII) can be prepared by taking a compound of formula (VII) where LG is a leaving group (such as chlorine or bromine) and protecting the sulfonamide, as for example the trimethylsilyethoxymethyl ether (SEM) or methoxymethyl ether (MOM) by the standard literature methods (such as SEM-chloride or MOM-chloride in a suitable solvent (such as tetrahydrofuran) with a suitable base (such as triethylamine) at a suitable temperature (such as 0-20° C.) to afford compound of the formula (VIII):

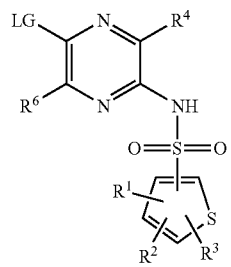
(VII)

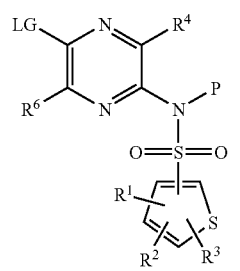
(VIII)

Compound of formula (VIII) could then be treated with compounds of formulae (IX):

$R^5$—H  (IX)

where $R^5$—H is a primary or secondary amine, thiol or alcohol as defined above (i.e. where $R^5$, is a group containing an X moiety where X is $NR^{13}$, O or S), in a suitable solvent (such as tetrahydrofuran or acetonitrile) with or without a suitable base (such as sodium hydride, caesium carbonate or triethylamine) at a suitable temperature ranging from 25-85° C. to afford compound of the formula (X):

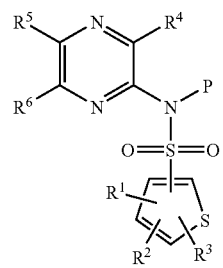
(X)

The protecting group (P) can then be removed by standard methods to afford compound of formula (I).

Compounds of structure (II) or (I), where $R^5$ is an optionally substituted aryl or heteroaryl ring as defined in the claims, can be prepared by taking a compound of formula (XI) or (VII) where LG is a suitable leaving group such as bromine, chlorine or iodine and reacting it with an aryl or heteroaryl boronic acid such as phenyl boronic acid, a palladium catalyst such as [1,1'-bis(diphenylphosphino)ferrocene]palladium (II) chloride, a suitable base such as cesium fluoride, sodium acetate or cesium carbonate and a suitable solvent such as methanol or ethanol and heating between 40-80° C.

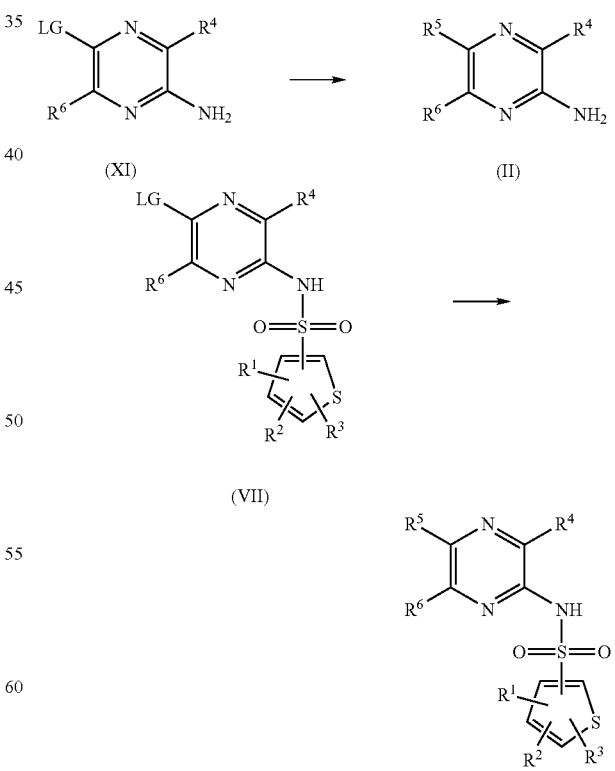

Compounds of formula (II) and (I) where $R^5$ or $R^6$ is $CO_2R^{13}$ can be prepared by reacting a compound of formula (II) or (I), where $R^5$ or $R^6$ is bromine or iodine, in a suitable solvent such as $R^{13}OH$ or dioxane containing $R^{13}OH$, a suitable tertiary amine such as triethylamine, a suitable palladium catalyst such as [1,1'-bis(diphenylphosphino)ferrocene]palladium (II) chloride under an atmosphere of carbon monoxide usually at 2-10 barr, ideally at 4-6 barr and at a temperature of 70-120° C.

Compounds of formula (II) and (I) where $R^5$ or $R^6$ is $CONR^{14}R^{15}$ can be prepared by reacting a compound of formula (II) or (I), where $R^5$ or $R^6$ is bromine or iodine, in a suitable solvent such as dioxane containing $NHR^{14}R^{15}$, a suitable tertiary amine such as triethylamine, a suitable palladium catalyst such as [1,1'-bis(diphenylphosphino)ferrocene]palladium (II) chloride under an atmosphere of carbon monoxide usually at 2-10 barr, ideally at 4-6 barr and at a temperature of 70-120° C.

Compounds of formula (I) where $R^5$ or $R^6$ is $CH_2OH$ can be prepared from compounds of formula (I) where $R^5$ or $R^6$ is $CO_2R^{13}$ by reduction using a suitable reducing agent such as lithium triethylborohydride in a suitable solvent such as tetrahydrofuran at a temperature of 0-10° C.

Compounds of formula (I) where $R^5$ or $R^6$ is CHO can be prepared from compounds of formula (I) where $R^5$ or $R^6$ is $CH_2OH$ by oxidation using a suitable oxidising agent such as manganese dioxide or pyridinium chlorochromate (PCC) in a suitable solvent such as tetrahydrofuran or dichloromethane at a temperature of 0-50° C.

Compounds of formula (I) where $R^5$ or $R^6$ is $CH(OH)R^{11}$ or CH(OH)(C1-5)alkyl can be prepared from compounds of formula (I) where $R^5$ or $R^6$ is CHO by reaction with a compound of formula (XII) where M is a metal such as magnesium or lithium in a suitable solvent such as tetrahydrofuran or diethyl ether at a temperature of 0-10° C.

$$C_{1-5}alkylM \text{ or } R^{11}M \quad (XII)$$

Intermediate compounds of formula (II) and (III) can be prepared using standard chemistry or are available commercially.

It will be appreciated by those skilled in the art that in the processes of the present invention certain functional groups such as hydroxyl or amino groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

The compounds of formula (I) above may be converted to a pharmaceutically acceptable salt or solvate thereof, preferably a basic addition salt such as sodium, potassium, calcium aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, furnarate, maleate, tartrate, citrate, oxalate, methanesulphonate or p-toluenesulphonate.

The compounds of formula (I) has activity as pharmaceuticals, in particular as modulators of chemokine receptor (especially CCR4) activity, and may be used in the treatment (therapeutic or prophylactic) of conditions/diseases in human and non-human animals which are exacerbated or caused by excessive or unregulated production of chemokines. Examples of such conditions/diseases include:

(1) (the respiratory tract) obstructive airways diseases including chronic obstructive pulmonary disease (COPD); asthma, such as bronchial, allergic, intrinsic extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia, (2) (bone and joints) gout, rheumatoid arthritis, seronegative spondyloarthropathies (including ankylosing spondylitis, psoriatic arthritis and. Reiter's disease), Behcet's disease, Sjogren's syndrome and systemic sclerosis;

(3) (skin) pruritis, scleroderma, otitus, psoriasis, atopical dermatitis, contact dermatitis and other eczmatous dermitides, seborrhoetic dermatitis, Lichen planus, Pemphigus, bullous Pemphigus, Epidermnolysis bullosa, urticaria, angiodermas, vasculitides, erythemas, cutaneous eosinophilias, uveitis, Alopecia greata and vernal conjunctivitis, lupus;

(4) (gastrointestinal tract) Coeliac disease, proctitis, eosinopilic gastro-eniteritis, mastocytosis, inflammatory bowel diseases such as Crohn's disease, ulcerative colitis, ileitis and enteritis, food-related allergies which have effects remote from the gut, e.g., migraine, rhinitis and eczema;

(5) (central and peripheral nervous system) Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal disorders, e.g. tropical spastic paraparesis, and stiff-man syndrome: paraneoplastic syndromes, e.g. cerebellar degeneration and encephalomyelitis; CNS trauma; migraine; stroke and correctum diseases such as meningitis.

(6) (other tissues and systemic disease) hepatitis, vasculitis, spondyloarthopathies, vaginitis, glomerulonephritis, myositis, athcrosclerosis, Acquired Immunodeficiency Syndrome (AIDS), lupus erythemfatosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) (allograft and xenograft rejection) acute and chronic following, for example, transplantation of kidney, heart liver, lung, bone marrow, skin and cornea; and chronic graft versus host disease;

(8) Cancer, carcinoma & tumour metastasis, including that of the bladder, breast, colon, kidney, liver, lung, ovary, pancreas, stomach, cervix, thyroid and skin, especially non-small cell lung cancer (NSCLC), malignant melanoma, prostate cancer and squamous sarcoma Hematopoietic tumors of lymphoid lineage, including acute lymphocytic leukemia, B cell lymphoma and Burketts lymphoma, Hodgkins Lymphoma, Acute Lymphoblastic Leukemia. Hematopoietic tumors of myeloid lineage, including acute and chronic myelogenous leukemias and promyelocytic leukemia Tumors of mesenchymal origin, including fibrosarcoma and rhaibdomyosarcoma, and other tumors, including melanoma, seminoma, tetratocarcinoma, neuroblastoma and glioma.

(9) All diseases that result from a general inbalance of the immune system and resulting in increased atopic inflammatory reactions.

(10) Cystic fibrosis, re-perfusion injury in the heart, brain, peripheral limbs and other organs.

(11) Burn wounds & chronic skin ulcers

(12) Reproductive Diseases (e.g. Disorders of ovulation, menstruation and implantation, Pre-term labour, Endometriosis)

(13) thrombosis

(14) infectious diseases such as HIV infection and other viral infections, bacterial infections.

Thus, the present invention provides a compound of formula (I), or a pharmaceutically-acceptable salt or solvate thereof, as hereinbefore defined for use in therapy.

Preferably the compound of the invention are used to treat diseases in which the chemokine receptor belongs to the CC chemokine receptor subfamily, more preferably the target chemokine receptor is the CCR4 receptor.

Particular conditions which can be treated with the compound of the invention are asthma, rhinitis and inflammatory skin disorders, diseases in which there are raised TARC, MDC or CCR4 levels. It is preferred that the compound of the invention is used to treat asthma and rhinitis, especially asthma.

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity, particularly CCR4 activity, is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CCR4) receptor, which comprises administering to a patient a therapeutically effective amount of a compound of formula (I), or a pharmaceutically acceptable salt or solvate thereof, as hereinbefore defined.

The invention also provides a method of treating a respiratory disease, such as asthma and rhinitis, especially asthma, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compound of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration is in the form of suppositories or transdermally. Preferably the compound of the invention is administered orally.

The following examples illustrate the invention.

EXAMPLE 1

N-(5-Bromo-3-methoxy-2-pyrazinyl)-5-chloro-2-thiophenesulphonamide

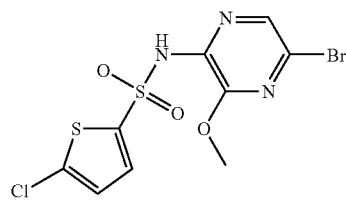

5-Bromo-3-methoxy-2-pyrazinamine (1.0 g) in 1,2-dimethoxyethane (10 mL) was added to a stirred suspension of sodium hydride (0.48 g of 60%) in 1,2-dimethoxyethane (10 mL) under nitrogen at room temperature. 5-Chloro-2-thienylsuphonyl chloride (1.1 g) in 1,2-dimethoxyethane (10 mL) was added dropwise over 30 minutes. After 1 hour, aqueous citric acid (50 mL of 5%) was added and the product extracted with ethyl acetate (X3). The combined extracts were washed with saturated brine, dried (MgSO$_4$) and the solvent was evaporated. Chromatograpy on silica eluting with dichloromethane gave the title compound as a white solid (1.2 g).

m/e 382/4/6 (M-1$^+$, 100%), $^1$H NMR (D6-DMSO) δ 8.08 (1H, s), 7.67 (1H, d), 7.24 (1H, d), 3.93 (3H, s).

EXAMPLE 2

N-(5-Bromo-3-ethoxy-2-pyrazinyl)-5-chloro-2-thiophenesulphonamide

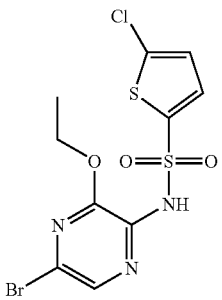

Prepared by the method of Example 1 from 5-bromo-3-ethoxy-2-pyrazinamine.

m/e 396/8/400 (M−1$^{+,}$ 100%), $^1$H NMR (D6-DMSO) δ 8.05 (1H, s), 7.69 (1H, d), 7.25 (1H, d), 4.35 (2H, q), 1.37 (3H, t).

EXAMPLE 3

N-(5-Bromo-3-methoxy-2-pyrazinyl)-4,5-dichloro-2-thiohenesulphonamide

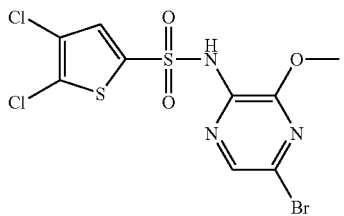

Prepared by the method of Example 1 from 4,5-dichlorothiophenesulphonyl chloride.

m/e 416/8/20/2 (M−1$^+$, 100%), $^1$H NMR (D6-DMSO) δ 8.08 (1H, s), 7.81 (1H, s), 3.93 (3H, s).

EXAMPLE 4

5-Chloro-N-(3-methoxy-5-phenyl-2-pyrazinyl)-2-thiophenesulphonamide

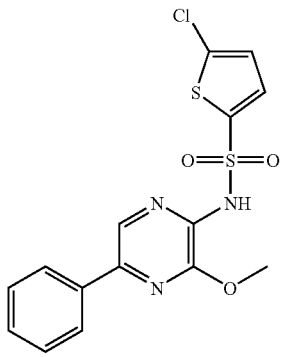

(a) 3-Methoxy-5-phenyl-2-pyrazinamine

5-Bromo-3-methoxy-2-pyrazinamine (0.31 g), cesium fluoride (0.8 g), benzeneboronic acid (0.36 g) and [1,1'-bis(diphenylphosphino)ferrocene]palladium (II) chloride (0.08 g) in methanol (7 mL) was heated at reflux for 2 hours. The solvent was evaporated and the residue purified by chromatography on silica eluting with toluene/ethyl acetate mixtures to give the sub-title compound (0.25 g).

m/e 202 (M+1$^+$, 100%), $^1$H NMR (D6-DMSO) δ 8.1 (1H, s), 7.91 (2H, d), 7.42 (2H, t) 7.28 (1H, t), 6.43 (2H, s), 4.0 (3H, s).

(b) 5-Chloro-N-(3-methoxy-5-phenyl-2-pyrazinyl)-2-thiophenesulphonamide

Prepared by the method of Example 1 from 3-methoxy-5-phenyl-2-pyrazinamine.

m/e 380/2 (M−1$^+$, 100%), $^1$H NMR (D6-DMSO) δ 8.5 (1H, s), 8.05 (2H, d), 7.70 (1H, d), 7.55-7.40 (3H, m), 7.25 (1H, d), 4.04 (3H, s).

EXAMPLE 5

N-(5-Bromo-3-phenoxy-2-pyrazinyl)$_5$-chloro-2-thiophenesulphonamide

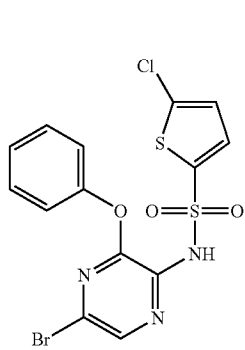

(a) 5-Bromo-3-phenoxy-2-pyrazinamine

Sodium phenoxide trihydrate (0.5 g) and 3,5-dibromo-2-pyrazinamine (0.5 g) in acetonitrile (20 mL) were heated at reflux for 7 hours. After cooling, water was added and the reaction mixture extracted with ethyl acetate (x2). The combined extracts were dried (MgSO$_4$) and the solvent evaporated to give the sub-title compound as a white solid.

m/e 266/8 (M+1$^+$, 25%), HPLC 98%.

$^1$H NMR (D6-DMSO) δ 7.75 (1H, s), 7.45 (2H, t), 7.25 (3H, m) and 6.84 (2H, s).

(b) N-(5-Bromo-3-phenoxy-2-pyrazinyl)-5-chloro-2-thiophenesulphonamide

Prepared by the method of Example 1 using the compound of Example 5a.

m/e 444/6/8 (M−1$^+$, 100%), $^1$H NMR (D6-DMSO) δ 8.24 (1H, s), 7.73 (1H, d), 7.47 (2H, t), 7.27 (4H, m).

EXAMPLE 6

N-(5-Bromo-3-methoxy-2-pyrazinyl)-2-thiophene-sulphonamide

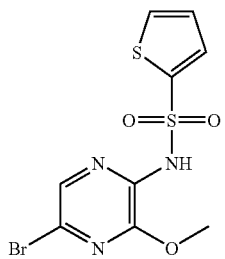

Prepared by the method of Example 1 from 2-thienylsulphonyl chloride.

m/e 348/50 (M−1⁺, 100%),

¹H NMR (D6-DMSO) δ 11.34 (1H, s), 8.03 (1H, s), 7.97 (1H, d), 7.80 (1H, d), 7.18-7.15 (1H, m), 3.93 (3H, s).

EXAMPLE 7

N-[5-Bromo-3-(2-furanylmethoxy)-2-pyrazinyl]-5-chloro-2-thiophenesulphonamide

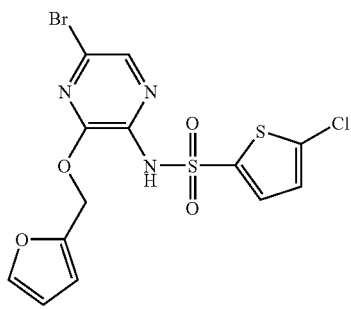

(a) 5-Bromo-3-(2-furanylmethoxy)-2-pyrazinamine

Prepared by the method of Example 20a from 2-furanylmethanol and sodium hydride in 1,2-dimethoxyethane and used directly in step 7b.

(b) N-[5-Bromo-3-(2-furanylmethoxy)-2-pyrazinyl]-5-chloro-2-thiophenesulphonamide Prepared by the method of Example 1 using the compound of Example 7a.

m/e 448/50/2 (M−1⁺, 100%),

¹H NMR (D6-DMSO) δ 8.12 (1H, s), 7.74 (1H, dd), 7.65 (1H, d), 7.23 (1H, d), 6.65 (1H, dd), 6.51 (1H, dd), 5.35 (2H, s).

EXAMPLE 8

5-Chloro-N-(3,5-dibromo-2-pyrazinyl)-2-thiophene-sulphonamide

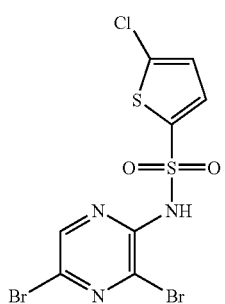

Prepared by the method of Example 1 from 3,5-dibromo-2-pyrazinamine.

m/e 430/2/4/6 (M−1⁺, 100%),

¹H NMR (D6-DMSO) δ 8.54 (1H, s), 7.62 (1H, d), 7.21 (1H, d).

EXAMPLE 9

5-Chloro-N-(3-methoxy-5-methyl-2-pyrazinyl)-2-thiophenesulphonamide

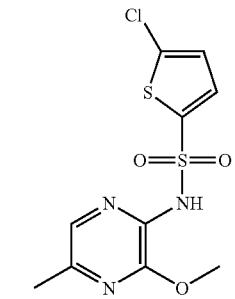

Prepared by the method of Example 1 from 3-methoxy-5-methyl-2-pyrazinamine.

m/e 318/20 (M−1⁺, 100%),

¹H NMR (D6-DMSO) δ 11.1 (1H, s), 7.77 (1H, s), 7.63 (1H, d), 7.22 (1H, d), 3.89 (3H, s), 2.33 (3H, s).

EXAMPLE 10

5-Chloro-N-(5-chloro-3-methoxy-2-pyrazinyl)-2-thiophenesulphonamide

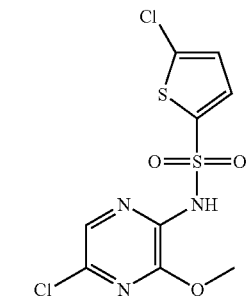

Prepared by the method of Example 1 from 5-chloro-3-methoxy-2-pyrazinamine.

m/e 338/40/2 (M−1⁺, 100%),

¹H NMR (D6-DMSO), δ 8.02 (1H, s), 7.67 (1H, d), 7.24 (1H, d), 3.93 (3H, s).

EXAMPLE 11

5-Bromo-N5-bromo-3-methoxy-2-pyrazinyl)₂-thiophenesulphonamide

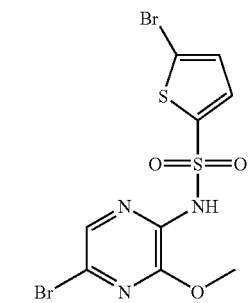

Prepared by the method of Example 1 from 5-bromo-2-thienylsulphonyl chloride.

m/e 426/8/430/2 (M−1+, 100%), $^1$H NMR (D6-DMSO) δ 8.07 (1H, s), 7.62 (1H, d), 7.33 (1H, d), 3.80 (3H, s).

EXAMPLE 12

5-Chloro-N-(6-chloro-3-methoxy-2-pyrazinyl)-2-thiophenesulphonamide

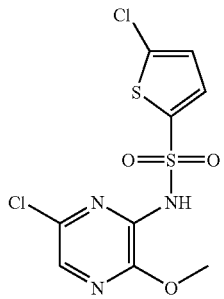

(a) 6-Chloro-3-methoxy-2-pyrazinamine and 3-bromo-6-methoxy-2-pyrazinamine 3-Bromo-6-chloro-2-pyrazinamine (0.13 g), sodium methoxide (2 mL of 25% in methanol) and methanol (3 mL) were heated at reflux for 3 hours. The solvent was evaporated and the residue was dissolved in ethyl acetate and brine. The organic layer was separated dried (MgSO$_4$), and the solvent was evaporated to give a mixture of the sub-title compounds.

(b) 5-Chloro-N-(6-chloro-3-methoxy 2-pyrazinyl)-2-thiophenesulphonamide Prepared by the method of Example 1 from a mixture of 6-chloro-3-methoxy-2-pyrazinamine and 3-bromo-6-methoxy-2-pyrazinamine. The title compound was separated and purified by chromatography on silica eluting with dichloromethane/methanol mixtures.

m/e 338/40/2 (M−1+, 100%), $^1$H NMR (D6-DMSO) δ 7.94 (1H, s), 7.67 (1H, d), 7.27 (1H, d), 3.91 (3H, s).

EXAMPLE 13

3-Bromo-N-(5-bromo-3-methoxy-2-pyrazinyl)-5-chloro-2-thiophenesulphonamide

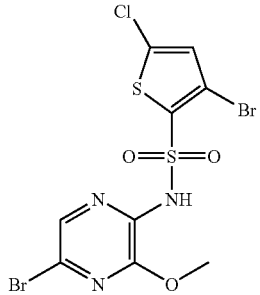

Prepared by the method of Example 1 from 3-bromo-5-chloro-2-thienylsulphonyl chloride.

m/e 460/2/4/6 (M−1+, 100%), $^1$H NMR (D6-DMSO) δ 7.95 (1H, s), 7.44 (1H, s), 3.93 (3H, s).

EXAMPLE 14

N-(5-Bromo-3-methoxy-2-pyrazinyl)3-thiophenesulphonamide

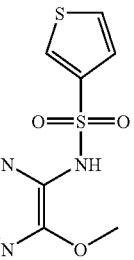

Prepared by the method of Example 1 from 3-thienylsulphonyl chloride.

m/e 350/2 (M+1+, 100%), $^1$H NMR (D6-DMSO) δ 11.08 (1H, s), 8.36-8.34 (1H, m), 7.97 (1H, s), 7.69 (1H, ddd), 7.47 (1H, ddd), 3.92 (3H, s).

EXAMPLE 15

5-Chloro-N5,6-dichloro-3-methoxy-2-pyrazinyl)-2-thiophenesulphonamide

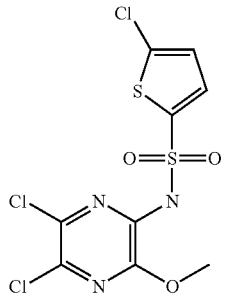

(a) 3,5,6-Trichloro-2-pyrazinamine

6-Chloro-2-pyrazinamine (0.42 g) and n-chlorosuccinimide (2.6 g) in chloroform (3 mL) was heated at reflux for 16 hours. Chromatography on silica eluting with dichloromethane gave the subtitle compound (0.68 g).

(b) 5,6-Dichloro-3-methoxy-2-pyrazinamine

Prepared by the method of Example 12a using 3,5,6-trichloro-2-pyrazinamine.

(c) 5-Chloro-N-(5,6-dichloro-3-methoxy-2-pyrazinyl)-2-thiophenesulphonamide

Prepared by the method of Example 1 from 5,6-dichloro-3-methoxy-2-pyrazinamine.

m/e 372/4/6/8 (M−1+, 100%), $^1$H NMR (D6-DMSO) δ 7.67 (1H, d), 7.27 (1H, d), 3.93 (3H, s).

EXAMPLE 16

5-Chloro-N-[5-bromo-3-(2-methoxyethoxy)-2-pyrazinyl]-2-thiophenesulphonamide

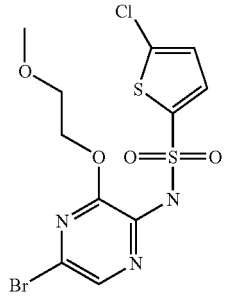

2-Methoxyethanol (0.04 g) was added to a stirred suspension of sodium hydride (0.05 g of 60%) in 1,2-dimethoxyethane (5 mL). After 10 minutes, 5-chloro-N-(3,5-dibromo-2-pyrazinyl)-2-thiophenesulphonamide (0.2 g) was added. After 30 minutes, 5% aqueous citric acid and ethyl acetate were added. The organic layer was separated dried (MgSO₄) and the solvent was evaporated. Chromatography on silica eluting with hexane/ethyl acetate gave the title compound.

m/e 426/8/30 (M−1⁺, 100%),

¹H NMR (D6-DMSO)δ 8.07 (1H, s), 7.68 (1H, d), 7.24 (1H, d) 4.44-4.41 (2H, m) 3.72-3.69 (2H, m), 3.31 (3H, s).

EXAMPLE 17

5-Chloro-N-[5-bromo-3-[2-(1-imidazolyl)ethoxy]-2-pyrazinyl]-2-thiophenesulphonamide

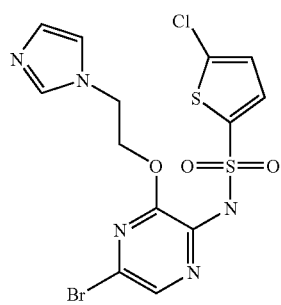

Prepared by the method of Example 20 using 2-(1-imidazolyl)ethanol.

m/e 464/6/8 (M−1⁺, 100%),

¹H NMR (D6-DMSO) δ 8.87 (1H, s), 7.74 (2H, d), 7.50 (1H, s), 7.37 (1H, d) 7.02 (1H, d), 4.55 (4H, s).

EXAMPLE 18

5-Bromo-N-(6-chloro-3-methoxy-2-pyrazinyl)-2-thiophenesulphonamide

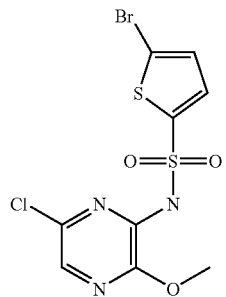

Prepared by the method of Example 1 from 6-chloro-3-methoxy-2-pyrazinamine and 5-bromothiophenesulphonyl chloride.

m/e 382/4/6 (M−1⁺, 100%),

¹H NMR (D6-DMSO) δ 7.95 (1H, s), 7.64 (1H, d) 7.38 (1H, d), 3.92 (3H, s).

EXAMPLE 19

5-Bromo-N-(5-chloro-3-methoxy-2-pyrazinyl)-2-thiophenesulphonamide

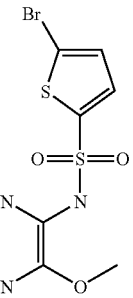

Prepared by the method of Example 1 from 5-chloro-3-methoxy-2-pyrazinamine and 5-bromothiophenesulphonyl chloride.

m/e 382/4/6 (M−1⁺, 100%),

¹H NMR (D6-DMSO) δ 8.01 (1H, s), 7.62 (1H, d) 7.33 (1H, d), 3.94 (3H, s).

EXAMPLE 20

5-Chloro-N-[6 chloro-3-(2-furanylmethoxy)-2-pyrazinyl]-2-thiophenesulphonamide a) 5-Chloro-N-(3-bromo-6-chloro-2-pyrazinyl)-2-thiophenesulphonamide

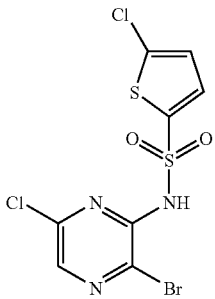

Prepared by the method of Example 1 using 3-bromo-6-chloro-2-pyrazinamine and 5-chloro-2-thienylsulphonyl chloride.

b) 5-Chloro-N-[6-chloro-3-(2-furanylmethoxy)-2-pyrazinyl]-2-thiophenesulphonamide

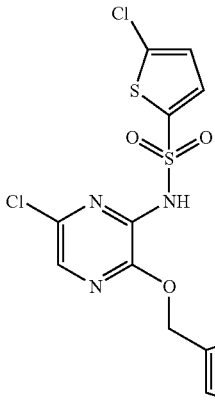

Sodium hydride (0.04 g of a 60% dispersion in oil) was added to furfurylalcohol (0.034 g) in 1,2-dimethoxyethane (1.0 mL). After 5 minutes 5-chloro-N-(3-bromo-6-chloro-2-pyrazinyl)-2-thiophenesulphonamide (0.1 g) was added and the mixture heated at 40° C. After 16 h, 5% aqueous citric acid (5.0 mL) was added and the mixture extracted with ethyl acetate (2×20 mL). The combined extracts were washed with brine, dried (MgSO$_4$) and the solvent evaporated. Chromatography on silica gel eluting with dichloromethane gave the title compound as a white solid (0.03 g).

m/e 404 (M–1$^+$, 100%), $^1$H NMR (D6-DMSO) δ 7.97 (1H, s), 7.73 (1H, dd), 7.66 (1H, d), 7.27 (1H, d), 6.63 (1H, dd), 6.49 (1H, dd), 5.34 (2H, s).

MP 130-133° C.

EXAMPLE 21

5-Chloro-N-[6-chloro-3-(5-methyl-3-isoxazolyl-methoxy)2-pyrazinyl]-2-thiophenesulphonamide

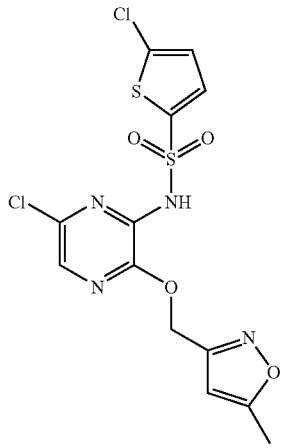

Prepared by the method of Example 20b using (5-methyl-3-isoxazolyl)methanol and 5-chloro-N-(3-bromo-6-chloro-2-pyrazinyl)-2-thiophenesulphonamide.

m/e 420 (M–1$^+$, 100%), $^1$H NMR (D6-DMSO)δ 7.95 (1H, s), 7.68 (1H, d), 7.28 (1H, d), 6.39 (1H, s), 5.40 (2H, s), 2.40 (3H, s).

MP 141-142° C.

EXAMPLE 22

5-Chloro-N-[6-chloro-3-(2-pyridinylmethoxy)-2-pyrazinyl[-2-thiophenesulphonamide

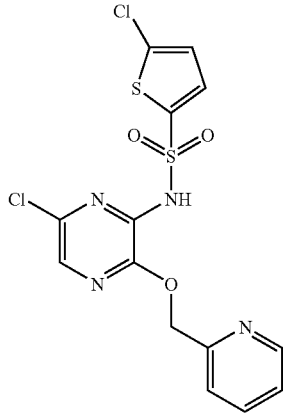

Prepared by the method of Example 20b using pyridine-2-methanol and 5-chloro-N-(3-bromo-6-chloro-2-pyrazinyl)-2-thiophenesulphonamide.

m/e 417 (M+1$^+$, 100%), $^1$H NMR (D6-DMSO) δ 8.56 (1H, d), 7.90 (1H, s), 7.86 (1H, d), 7.68 (1H, d), 7.62 (2H, d), 7.39 (1H, dd), 7.27 (1H, d), 5.47 (2H, s).

MP 171-172° C.

EXAMPLE 23

5-Chloro-N-[5-methyl-3-(3-pyridinylmethoxy)-2-pyrazinyl]-2-thiophenesulphonamide a)  5-Chloro-N-(3-bromo-5-methyl-2-pyrazinyl)-2-thiophenesulphonamide

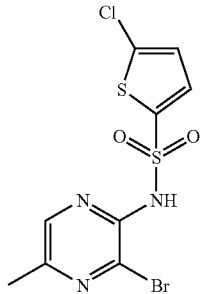

Prepared by the method of Example 1 using 3-bromo-5-methyl-2-pyrazinamine and 5-chloro-2-thienylsulphonyl chloride b)  5-Chloro-N-[5-methyl-3-(3-pyridinylmethoxy)-2-pyrazinyl]-2-thiophenesulphonamide

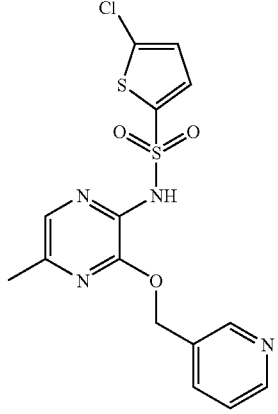

Prepared by the method of Example 20b using pyridine-3-methanol and 5-chloro-N-(3-bromo-5-methyl-2-pyrazinyl)-2-thiophenesulphonamide.

m/e 397 (M+1$^+$, 100%), $^1$H NMR (D6-DMSO)δ 8.77 (1H, br s), 8.55 (1H, d), 7.94 (1H, dt), 7.81 (1H, br s), 7.63 (1H, d), 7.42 (1H, dd), 7.20 (1H, d), 5.41 (2H, s), 2.34 (3H, s) MP 204-205° C.

EXAMPLE 24

5-Chloro-N-[5-methyl-3-(3-pyridazinylmethoxy)-2-pyrazinyl]-2-thiophenesulphonamide

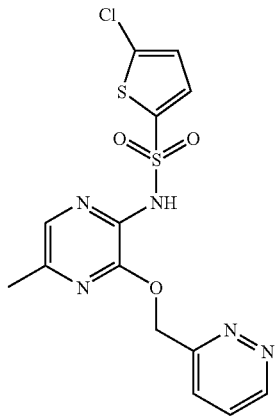

Prepared by the method of Example 20b using pyridazine-3-methanol and 5-chloro-N-(3-bromo-5-methyl-2-pyrazinyl)-2-thiophenesulphonamide (Example 23a).

m/e 398 (M+1$^+$, 100%), $^1$H NMR (D6-DMSO)δ 11.28 (1H, br s), 9.21 (1H, dd), 7.95 (1H, d), 7.85 (1H, br s), 7.78 (1H, dd), 7.65 (1H, d), 7.21 (1H, d), 5.65 (2H, s), 2.32 (3H, s).

MP 179-181° C.

EXAMPLE 25

5-Chloro-N-[3-(2-pyridinylmethoxy)-2-pyrazinyl]-2-thiophenesulphonamide a) 5-Chloro-N-(3-chloro-2-pyrazinyl)-2-thiophenesulphonamide,

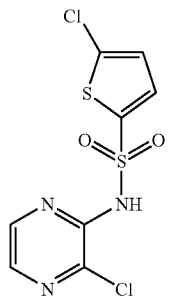

2,3-Dichloropyrazine (0.8 g), 5-chloro-2-thienylsulphonamide (1.1 g) and potassium carbonate (2.5 g) in N,N-dimethylformamide (20 mL) was heated at 75° C. After 16 h, 5% aqueous citric acid (10.0 mL) was added and the mixture extracted with ethyl acetate (2×20 mL). The combined extracts were washed with brine, dried (MgSO$_4$) and the solvent evaporated. Chromatography on silica gel eluting with ethyl acetate/isohexane mixtures gave the title compound (0.5 g).

b) 5-Chloro-N-[3-(2-pyridinylmethoxy)-2-pyrazinyl]-2-thiophenesulphonamide

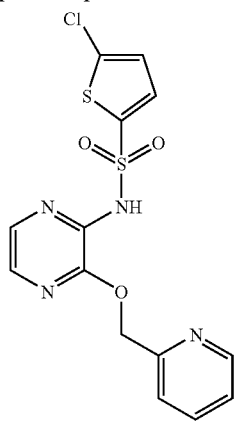

Prepared by the method of Example 20b using pyridine-2-methanol and 5-chloro-N-(3-chloro-2-pyrazinyl)-2-thiophenesulphonamide with reaction mixture heated at 70° C. for 4 h.

m/e 383 (M+1$^+$, 100%), $^1$HNMR (D6-DMSO) δ 8.56 (1H, d), 7.91 (1H, br s), 7.87-7.80 (2H, m), 7.70 (1H, d), 7.61 (1H, d), 7.35-7.30 (1H, m), 7.23 (1H, d), 5.48 (2H s).

MP 109-110° C.

EXAMPLE 26

5-Chloro-N-(3-methoxy-2-pyrazinyl)-2-thiophenesulphonamide

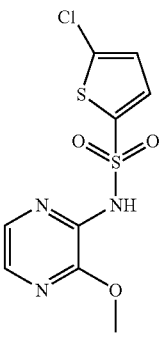

5-Chloro-N-(3-chloro-2-pyrazinyl)-2-thiophenesulphonamide (Example 25a) (0.03 g) in sodium methoxide in methanol (1.5 mL of a 10% solution) was heated at 85° C. After 4 h, 5% aqueous citric acid (10.0 mL) was added and the mixture extracted with ethyl acetate (2×30 mL). The combined extracts were washed with brine, dried (MgSO$_4$) and the solvent evaporated. Chromatography on silica gel eluting with ethyl acetate/isohexane mixtures gave the title compound as a white solid (0.026 g).

m/e 304 (M−1$^+$, 100%), $^1$H NMR (D6-DMSO) δ 7.90-7.80 (2H, m), 7.68 (1H, d), 7.23 (1H, d), 3.91 (3H, s).

MP 119-120° C.

EXAMPLE 27

5-Chloro-N-(5,6-dimethyl-3-methoxy-2-pyrazinyl)-2-thiophenesulphonamide

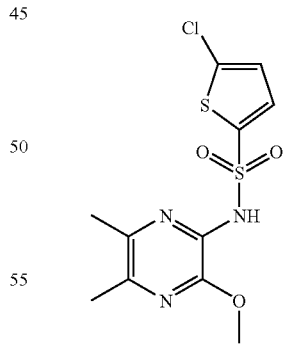

Prepared by the method of Example 1 using 3-methoxy-5,6-dimethyl-2-pyrazinamine and 5-chloro-2-thienylsulphonyl chloride.

m/e 334 (M+1$^+$, 100%), $^1$H NMR(CDCl$_3$) δ 7.69 (1H, d), 7.44 (1H, br s), 6.90 (1H, d), 3.94 (3H, s), 2.40 (3H, s), 2.34 (3H, s).

MP 95-96° C.

EXAMPLE 28

N-[5-Chloro-3-methoxy-2-pyrazinyl]-5-methyl-2-thiophenesulphonamide

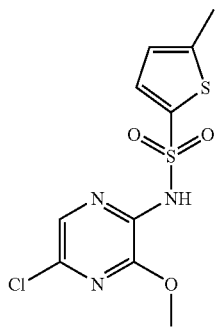

Prepared by the method of Example 1 using 5-methylthiophenesulphonyl chloride and 5-chloro-3-methoxy-2-pyrazinamine.

m/e 318 (M−1$^+$, 100%), $^1$H NMR (D6-DMSO) δ 11.27 (1H, br s), 7.96 (1H, s), 7.61 (1H, d), 6.87 (1H, d), 3.93. (3H, s), 2.48 (3H, s).

EXAMPLE 29

5-Methyl-N-[5-methyl-3-methoxy-2-pyrazinyl]-2-thiophenesulphonamide

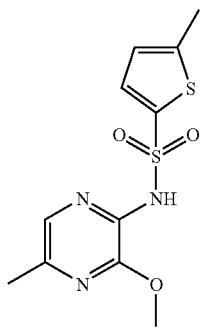

Prepared by the method of Example 1 using 5-methylthiophenesulphonyl chloride and 3-methoxy-5-methyl-2-pyrazinamine.

m/e 298 (M−1$^+$, 100%), $^1$H NMR, (6-DM SO) δ 10.79 (1H, s), 7.72 (1H, s), 7.57 (1H, d), 6.86 (1H, d), 3.88 (3H, s), 2.48 (3H, s), 2.31 (3H, s).

EXAMPLE 30

N-[5-{(2-Aminoethyl)sulpanyl}-3-methoxy-2-pyrazinyl]-5-chloro-2-thiophenesulphonamide a) N-[5-bromo-3-methoxy-2-pyrazinyl]-5-chloro-N-[(2-trimethylsilanylethoxy)methyl-9-thiophenesulphonamide

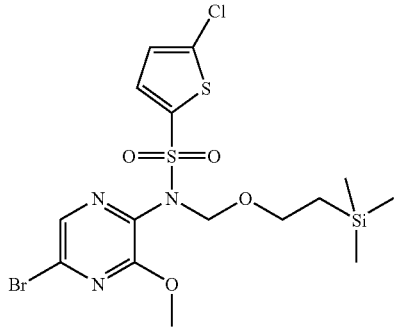

A mixture N-(5-Bromo-3-methoxy-2-pyrazinyl)-5-chloro-2-thiophenesulphonamide (Example 1) (0.40 g), diisopropylethylamine (0.26 g) and [2-(chloromethoxy)ethyl]trimethylsilane (0.25 g) in dichloromethane (50 mL) was stirred at room temperature. After 2 h, the solution was washed with water, dried (MgSO$_4$) and evaporated. Chromatography on silica gel eluting with ethyl acetate/isohexane mixtures gave the title compounds a white solid (0.40 g).

$^1$H NMR (CDCl$_3$) δ 8.19 (1H, s), 7.58 (1H, d), 7.00 (1H, d), 5.2 (2H, s), 4.1 (3H, s), 3.40-3.60 (2H, m), 0.75-0.85 (2H, m), 0.0 (9H, s).

b) N-[5-{(2-Aminoethyl)sulpanyl}-3-methoxy-2-pyrazinyl]-5-chloro-2-thiophenesulphonamide

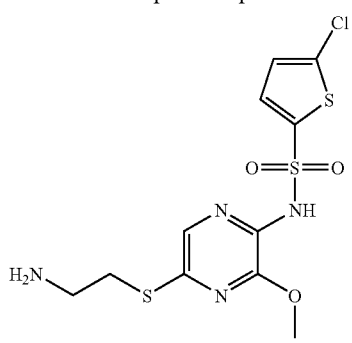

The product from step 30a (0.26 g), 2-mercaptoethylamine hydrochloroide (0.07 g) and cesium carbonate (0.41 g) in acetonitrile (10 ml) was stirred at room temperature and under nitrogen for 20 hours. The reaction mixture was partitioned between ethyl acetate and water. The ethyl acetate solution was then washed with brine, dried (MgSO$_4$) and evaporated. Chromatography on silica eluting with methanol/dichloromethane, 1/10 gave N-[5-{(2-Aminoethyl)sulpanyl}-3-methoxypyrazin-2-yl]-5-chloro-N-[(2-trimethylsilanylethoxy)methyl]-2-thiophenesulphonamide (0.2 g).

This compound was dissolved in trifluoroacetic acid (5 mL) at room temperature. After 5 minutes, toluene (30 ml) was added and the mixture evaporated. Diethyl ether was added and the product crystallised to give a white solid (0.17 g).

m/e 379(M−1$^+$).

$^1$H NMR (D6-DMSO) δ 7.90 (2H, br s), 7.90 (1H, s), 7.63 (1H, d), 7.23 (1H, d), 3.95 (3H, s), 3.30 (2H, t), 3.11 (2H, m).

MP 192-194° C.

EXAMPLE 31

5-Chloro-N-[5-cyano-3-methoxy-2-pyrazinyl]-2-thiophenesulphonamide

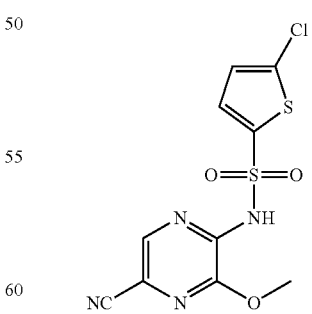

The product from Example 1 (0.1 g), zinc cyanide (0.02 g) and tetrakis(triphenylphosphine)palladium (0) (0.015 g) in dry N,N-dimethylformamide (5 mL) (deoxygenated by bubbling nitrogen through the solution for 10 minutes) was heated under nitrogen at 80° C. for 9 hours and then the reaction mixture was evaporated to dryness under reduced pressure. Chromatography on silica eluting with ethyl acetate/iso-hexanes, 1/1 gave the title compound (0.05 g).

m/e 329 (M−1+).

$^1$H NMR (DMSO) δ 8.41 (2H, s), 7.70 (1H, d), 7.25 (1H, d), 3.93 (3H, s).

MP 218-219° C.

EXAMPLE 32

N-[5-Bromo-3-(4-methoxybenzyloxy)pyrazin-2-yl]-5-chloro-2-thiophenesulphonamide

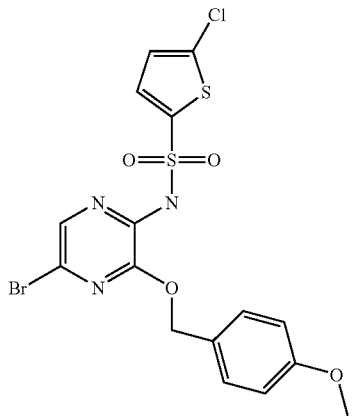

Prepared by the method of Example 20b using 5-chloro-N-(3,5-dibromo-2-pyrazinyl)-2-thiophenesulphonamide (Example 8) (0.32 g) and 4-methoxybenzylalcohol (0.1 g) to give the product (0.32 g).

m/e 490 (M+1+).

$^1$H NMR (DMSO) δ 8.09 (1H, s), 7.65 (1H, d), 7.45 (2H, d), 7.23 (1H, d), 6.95 (2H, d), 5.30 (2H, d), 3.76 (3H, s).

Pharmacological Data

FMAT Whole Cell Binding Assay

Cells

CHO-K1 cells stably expressing the human recombinant CCR4 receptor (Euroscreen; Brussels, Belgium) were cultured in NUT.MIX.F__12(HAM) medium with glutamax-1, containing 10% (v/v) foetal bovine serum and 400 μg ml$^{-1}$ geneticin.

Cells were harvested at approximately 70% confluence by treatment with a cell dissociation buffer, and seeded at 5×10$^3$ cells/100 μl culture medium into wells of a black Costar clear-bottomed 96-well microtitre plates. Plates were incubated overnight at 37° C. in 5% CO$_2$ and used the following day.

Assay

Before use, the cell plates were washed twice with 100 μl Hanks balanced salt solution (HBSS). To each well was then added 65 μl of HBSS, 10 μL of 10% DMSO in HBSS±test compound and then 25 μL of 2.8 nM FB-MDC (Applied Biosystems). This fluorescent probe was prepared from a 10 μM stock in 0.08% (v/v) TFA/16% (v/v) acetonitrile, diluted into HBSS.

After two hours incubation in the dark at room temperature, the plates were analysed in an FMAT8100 reader (Applied Biosystems) to measure fluorescence that was associated with binding of FB-MDC to the cells. Compound activity was determined as an pIC$_{50}$ [log(concentration of compound that results in 50% inhibition)], comparing fluorescence in control and background wells.

Typical Data

Fluorescence (ctrl)=1200

Fluorescence (bkg)=0

| | | Mean |
|---|---|---|
| Example 1 | pIC$_{50}$ | 7.4 |
| Example 23 | pIC$_{50}$ | 8.0 |
| Example 16 | pIC$_{50}$ | 6.2 |

All the compounds of the examples have a pIC$_{50}$ of less than 5.0.

The invention claimed is:

1. A compound of formula (I) or a pharmaceutically acceptable salt thereof:

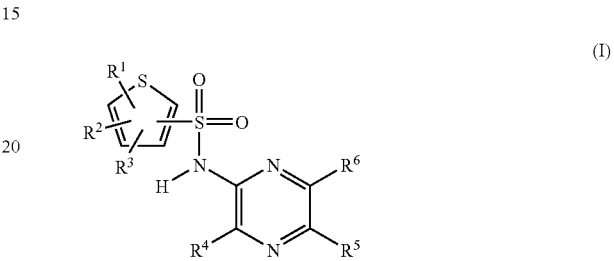

(I)

in which:

R$^1$, R$^2$ and R$^3$ are independently hydrogen, halogen, cyano, CF$_3$, or C$_{1-6}$ alkyl;

R$^4$ is halogen, CO$_2$R$^{12}$,

C$_{1-6}$ alkoxy where the alkyl group may form a 3-6 membered saturated ring or may be substituted with 1-3 fluorine atoms or a cyano group;

C$_{3-6}$ alkenyloxy or C$_{3-6}$ alkynyloxy where either may be optionally substituted with hydroxy or NR$^{14}$R$^{15}$;

OC$_{1-6}$ alkyl-X—C$_{1-6}$ alkyl where the alkyl groups may form a 3-6 membered saturated ring;

OC$_{1-6}$ alkylR$^{11}$, or OC$_{2-6}$ alkyl-X—R$^{11}$ where the alkyl group may form a 3-6 membered saturated ring and is optionally substituted with 1-3 groups selected from hydroxy, halogen, NR$^{14}$R$^{15}$, SR$^{13}$, S(O)$_2$R$^{13}$, S(O)$^{13}$;

OC$_{1-6}$ alkylR$^{16}$;

R$^5$ and R$^6$ are independently hydrogen, cyano, halogen, CO$_2$R$^{12}$, CONR$^{14}$R$^{15}$;

C$_{1-6}$ alkyl optionally substituted by hydroxy, NR$^{14}$R$^{15}$, or 1-3 fluorines;

C$_{1-6}$ alkylR$^{11}$ or XCH(R$^{11}$)C$_{1-6}$ alkyl or XCH(R$^{16}$)C$_{1-6}$ alkyl where the alkyl group may be optionally substituted with 1-3 groups selected from hydroxy, and NR$^{14}$R$^{15}$;

NR$^{14}$R$^{15}$; N(R$^{11}$)R$^{11}$; X—(CH$_2$)qNR$^{14}$R$^{15}$; (CH$_2$)nNR$^{14}$R$^{15}$;

C$_{3-6}$ alkynyl or C$_{3-6}$ alkenyl optionally branched and optionally substituted with 1-3 groups selected from hydroxy, cyano, halogen and =O;

R$^{11}$; X—R$^{11}$; X—R$^{12}$; X—C$_{1-6}$alkylR$^{16}$; X—R$^{16}$; X—(CH$_2$)nCO$_2$R$^{12}$; X—(CH$_2$)nCONR$^{14}$R$^{15}$;

X—(CH$_2$)nR$^{11}$; X—(CH$_2$)nCN; X—(CH$_2$)qOR$^{12}$; (CH$_2$)nOR$^{12}$;

(CH$_2$)n-X—R$^{11}$; X—(CH$_2$)qNHC(O)NHR$^{12}$; X—(CH$_2$)qNHC(O)R$^{12}$;

X—(CH$_2$)qNHS(O)$_2$R$^{12}$; X—(CH$_2$)qNHS(O)$_2$R$^{11}$; X—C$_{3-6}$ alkenyl; X—C$_{3-6}$ alkynyl;

n is 1, 2, 3, 4 or 5;

q is 2, 3, 4, 5 or 6;

X is NR$^{13}$, O, S, S(O), S(O)$_2$;

R¹¹ is
  an aryl group or a 5-7 membered heteroaromatic ring containing 1-4 heteroatoms selected from nitrogen, oxygen or sulphur each of which can be optionally substituted by 1-3 groups selected from halogen, C(O)NR¹⁴R¹⁵, C(O)OR¹², hydroxy, =O,=S, CN, NO₂,
  NR¹⁴R¹⁵, X(CH₂)qNR¹⁴R¹⁵, (CH₂)nNR¹⁴R¹⁵, (CH₂)nOH, SR¹³, S(O)R¹³, S(O)₂R¹³ C₁₋₆ alkyl-X—C₁₋₆ alkyl, C₁₋₆ alkyl or C₁₋₆ alkoxy where the alkyl group may form a 3-6 membered ring or is optionally substituted with 1-3 groups selected from hydroxy, halogen, NR¹⁴R¹⁵, SR¹³, S(O)R¹³, S(O)₂R¹³;
R¹² and R¹³ are independently hydrogen or C₁₋₆ alkyl where the alkyl group may be substituted with 1-3 fluorine atoms or may form a saturated 3-6 membered ring;
R¹⁴ and R¹⁵ are independently hydrogen, C₁₋₆ alkyl, C₃₋₆ cycloalkyl or (CH₂)qOH, or R¹⁴ and R¹⁵ together with the nitrogen atom to which they are attached form a 4-8 membered saturated ring containing 1-3 heteroatoms selected from nitrogen, oxygen and sulphur and optionally substituted by C₁₋₆ alkyl, C₁₋₆ alkyl-OH, or hydroxy; and
R¹⁶ is a 4-8 membered saturated ring containing 1-3 heteroatoms selected from nitrogen, oxygen or sulphur and optionally substituted with 1-3 groups selected from hydroxy, cyano, halogen and =O.

2. The compound according to claim 1 in which the thienyl moiety is linked to the sulphonamide at the 2-position of the ring.

3. The compound according to claim 1 in which R¹, R² and R³ are all hydrogen or two are hydrogen and the other is chloro, bromo or methyl.

4. The compound according to claim 1 in which R⁴ is C₁₋₆, alkoxy, phenoxy, 2-furanylmethoxy, bromo, 2-methoxyethoxy, (5-methyl-3-isoxazolyl)methoxy, 2-pyridylmethoxy, 3-pyridazinylmethoxy, 2-(1-imidazolyl)ethoxy or 4-methoxyphenylmethoxy.

5. The compound according to claim 1 in which R⁵ is hydrogen, halogen, phenyl, C₁₋₆ alkyl, cyano or 2-ammothanethiol.

6. The compound according to claim 1 in which R⁶ is hydrogen, C₁₋₆ alkyl or halogen.

7. The compound according to claim 1 which is:
N-(5-Bromo-3-methoxy-2-pyrazinyl)-5-chloro-2-thiophenesulphonamide
N-(5-Bromo-3-ethoxy-2-pyrazinyl)-5-chloro-2-thiophenesulphonamide
N-(5-Bromo-3-methoxy-2-pyrazinyl)-4,5-dichloro-2-thiophenesulphonamide
5-Chloro-N-(3-methoxy-5-phenyl-2-pyrazinyl)-2-thiophenesulphonamide
N-(5-Bromo-3-phenoxy-2-pyrazinyl)-5-chloro-2-thiophenesulphonamide
N-(5-Bromo-3-methoxy-2-pyrazinyl)-2-thiophenesulphonamide  N-[5-Bromo-3-(2-furanylmethoxy)-2-pyrazinyl]-5-chloro-2-thiophenesulphonamide
5-Chloro-N-(3     ,5-dibromo-2-pyrazinyl)-2-thiophenesulphonamide
5-Chloro-N-(3-methoxy-5-methyl-2-pyrazinyl)-2-thiophenesulphonamide
5-Chloro-N-(5-chloro-3-methoxy-2-pyrazinyl)-2-thiophenesulphonamide
5-Bromo-N-(5-bromo-3-methoxy-2-pyrazinyl)-2-thiophenesulphonamide
5-Chloro-N-(6-chloro-3-methoxy-2-pyrazinyl)-2-thiophenesulphonamide
3-Bromo-N-(5-bromo-3-methoxy-2-pyrazinyl)-5-chloro-2-thiophenesulphonamide
N-(5-Bromo-3-methoxy-2-pyrazinyl)-3-thiophenesulphonamide
5-Chloro-N-(5    ,6-dichloro-3-methoxy-2-pyrazinyl)-2-thiophenesulphonamide
5-Chloro-N-[5-bromo-3-(2-methoxyethoxy)-2-pyrazinyl]-2-thiophenesulphonamide
5-Chloro-N-[5-bromo-3-[2-(1-imidazolyl)ethoxy]-2-pyrazinyl]-2-thiophenesulphonamide
5-Bromo-N-(6-chloro-3-methoxy-2-pyrazinyl)-2-thiophenesulphonamide
5-Bromo-N-(5-chloro-3-methoxy-2-pyrazinyl)-2-thiophenesulphonamide
5-Chloro-N-[6-chloro-3-(2-furanylmethoxy)-2-pyrazinyl]-2-thiophenesulphonamide
5-Chloro-N-[6-chloro-3-(5-methyl-3    -isoxazolylmethoxy)-2-pyrazinyl]-2-thiophenesulphonamide
5-Chloro-N-[6-chloro-3-(2-pyridinylmethoxy)-2-pyrazinyl]-2-thiophenesulphonamide
5-Chloro-N-[5-methyl-3-(3-pyridinylmethoxy)-2-pyrazinyl]-2-thiophenesulphonamide
5-Chloro-N-[5-methyl-3-(3-pyridazinylmethoxy)-2-pyrazinyl]-2-thiophenesulphonamide
5-Chloro-N-[3-(2-pyridinylmethoxy)-2-pyrazinyl]-2-thiophenesulphonamide
5-Chloro-N-(3-methoxy-2-pyrazinyl)-2-thiophenesulphonamide
5-Chloro-N-(5,6-dimethyl-3     -methoxy-2-pyrazinyl)-2-thiophenesulphonamide
N-     [5-Chloro-3-methoxy-2-pyrazinyl]-5-methyl-2-thiophenesulphonamide
5-Methyl-N-[5-methyl-3-methoxy-2-pyrazinyl]-2-thiophenesulphonamide
N-[5-{(2-Aminoethyl)sulpanyl}-3-methoxypyrazin-2-yl]-5-chloro-2-thiophenesulphonamide
5-Chloro-N-[5-cyano-3-methoxypyrazin-2-yl]-2-thiophenesulphonamide
N-[5-Bromo-3-(4-methoxybenzyloxy)pyrazin-2-yl]-5-chloro -2-thiophenesulphonamide or a pharmaceutically acceptable salt thereof.

8. A compound of formula (IA)

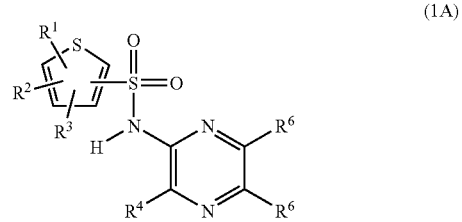

(1A)

in which:
R¹, R² and R³ are independently hydrogen, C₁₋₆ alkyl or halogen;
R⁴ is halogen, C₁₋₆ alkoxy or OR⁹;
R⁵ and R⁶ are independently hydrogen, halogen, C₁₋₆ alkoxy, C₁₋₆ alkylthio, cyano,R⁹, OR⁹, NR⁹R¹⁰, SR⁹, S(CH₂)ₙCO₂H, S(CH₂)ₙCO₂R¹², S(CH₂)ₙCONR¹²R¹³, S(CH₂)ₙR¹¹ or a 5- to 7-membered heteroaromatic or saturated ring containing 1 to 3 heteroatoms selected from nitrogen, oxygen and sulphur;
n is 1,2 or 3;
R⁹ and R¹⁰ are independently hydrogen, C₁₋₆ alkyl optionally substituted by hydroxy, C₁₋₆ alkoxy or NHCOC₁₋₆ alkyl, or $R^9$ and $R^{10}$ optionally substituted aryl, $C_{1-6}$ alkyl-aryl or $C_{1-6}$ alkyl-$R^{11}$ or $R^9$ and $R^{10}$ together with the nitrogen atom to which they are attached form a 4- to 8-membered saturated ring containing 1 to 3 heteroatoms selected from nitrogen, oxygen and sulphur and optionally substituted by $C_{1-6}$ alkyl or $C_{1-6}$ alkyl-OH; and $R^{11}$ is a 5- to 7-membered heteraromatic ring containing 1 to 3 heteroatoms selected from nitrogen, oxygen and sulphur and optionally substituted by $C_{1-6}$ alkyl; and $R^{12}$ and $R^{13}$ are independently hydrogen or $C_{1-6}$ alkyl.

9. The compound according to claim 8 in which $R^1$, $R^2$ and $R^3$ are all hydrogen or two are hydrogen and the other is chloro or methyl.

10. The compound according to claim 8 in which $R^4$ is $C_{1-6}$ alkoxy, phenoxy, 2-furanylmethoxy, bromo, 2-methoxyethoxy, (5-methyl-3-isoxazolyl)methoxy, 2-pyridylmethoxy, 3-pyridazinylmethoxy, methoxy or 2-(1-imidazolyl)ethoxy.

11. The compound according to claim 8 in which $R^5$ is halogen, phenyl or $C_{1-6}$ alkyl.

12. The compound according to claim 8 in which $R^6$ is hydrogen, $C_{1-6}$ alkyl and halogen.

13. A process for the preparation of a compound of formula (I) as claimed in claim 1 which comprises reaction of a compound of formula (II):

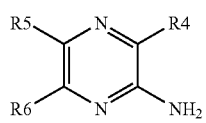

where $R^4$, $R^5$ and $R^6$ are as defined in formula (I) or are protected derivatives thereof with a compound of formula (III):

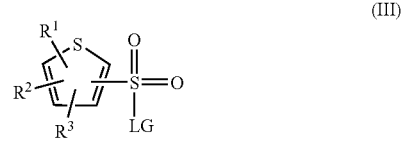

where $R^1$, $R^2$ and $R^3$ are as defined in formula (I) or are protected derivatives thereof and LG is a leaving group, and optionally thereafter removing any protecting groups, forming a pharmaceutically acceptable salt.

14. A pharmaceutical composition comprising a compound of formula (I), or a pharmaceutically acceptable salt thereof, as claimed in claim 1 in association with a pharmaceutically acceptable adjuvant, diluent or carrier.

15. A process for the preparation of a pharmaceutical composition as claimed in claim 14 which comprises mixing a compound of formula (I), or a pharmaceutically acceptable salt thereof, as claimed in claim 1 with a pharmaceutically acceptable adjuvant, diluent or carrier.

16. A method of treating asthma in a patient in need thereof, which comprises administering to the patient a therapeutically effective amount of a compound of formula (I), or a pharmaceutically acceptable salt thereof, as claimed in claim 1.

* * * * *